United States Patent [19]

Jaffe

[11] Patent Number: 5,028,643

[45] Date of Patent: Jul. 2, 1991

[54] TETRABENZODIAZADIKETOPERYLENE PIGMENT

[75] Inventor: Edward E. Jaffe, Wilmington, Del.

[73] Assignee: Ciba-Geigy Corporation, Ardsley, N.Y.

[21] Appl. No.: 372,401

[22] Filed: Jun. 27, 1989

[51] Int. Cl.$^5$ .................. C08K 5/3437; C07D 471/02; C07D 221/18

[52] U.S. Cl. ......................... 524/90; 546/28; 546/58

[58] Field of Search ........................ 546/28, 58; 524/90

[56] References Cited

U.S. PATENT DOCUMENTS 4,405,734  9/1983  Fuchs et al. ........................ 524/90

FOREIGN PATENT DOCUMENTS 63-193960  8/1988  Japan ........................ 546/28

OTHER PUBLICATIONS

Kitahara et al., J. Heterocyclic Chem. 25, 1063-1065-/7-8/88).
Derwent Publications et al.; 88-267171/38; Aug. 1988.

*Primary Examiner*—Lewis T. Jacobs
*Attorney, Agent, or Firm*—Harry Falber

[57] ABSTRACT

5,15-Diaza-5b, 15b-dihydrotetrabenzo[a,g,j,p] perylene-6,16-dione, a process for the preparation thereof and its suitability for use as a pigment for coloring a wide variety of organic materials.

5 Claims, No Drawings

TETRABENZODIAZADIKETOPERYLENE PIGMENT

A wide variety of perylene and quinacridone derivatives have been known to those skilled in the art as pigments for high molecular weight organic materials. Additional derivatives with good pigmentary properties continue, however, to be sought.

A new perylene derivative having desirable pigmentary properties has now been discovered. Thus, the derivative corresponds to the formula

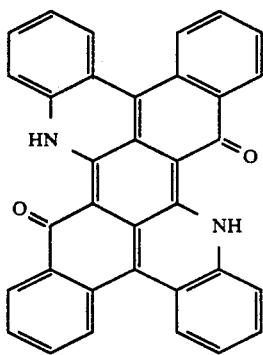

and is named 5,15-diaza-5$b$, 15$b$-dihydrotetrabenzo[a,g,j,p] perylene-6,16-dione.

The indicated colored compound is obtained by condensing di($C_1$–$C_3$alkyl)succinylsuccinate, preferably dimethyl succinylsuccinate, with 2-aminobenzophenone in a solvent such as an aliphatic alcohol of 1 to 4 carbon atoms, a glycol or glycol ether, an open chain or cyclic amide, or an aromatic solvent such as xylene or Dowtherm. The reaction is conducted at elevated temperatures either under reflux or under vacuum to remove volatile by-products. for the higher boiling solvents, and in the presence of catalytic amounts of mineral acid or aliphatic organic acids. The resulting intermediate product is deemed to correspond to the formula

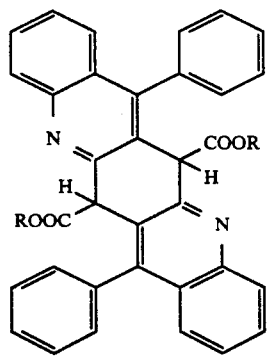

wherein R is $C_1$–$C_3$ alkyl.

The intermediate is then cyclized by pyrolysis either neat at high temperatures or in a relatively high boiling organic solvent to precipitate the pigment as a black crystalline crude product melting at a temperature higher than 300° C.

The isolated product is a black-violet pigment exhibiting low solubility in organic solvents making it suitable for use in plastics and fibers, distinct pigmentary coloring properties, minimal susceptibility to fading upon exposure to solar radiation and variable hiding power depending on its state of subdivision or particle size.

Pigmented systems which contain the pigment as a component of mixtures of substances, possibly in addition to other components, include: pastes, flush pastes, preparations, printing colors, distempers, binder colors or lacquers and varnishes of all kinds, such as physically and oxidatively drying lacquers and varnishes, acid, amine and peroxide curing varnishes or polyurethane varnishes. The pigment may also be present in other high molecular weight materials including synthetic, semisynthetic or natural macromolecular substances, such as thermoplastic resins, e.g., polyvinyl chloride, polystyrene, polyethylene, polyesters, phenoplasts, aminoplasts and rubber. The pigment may also be present in admixture with natural, regenerated or synthetic fibers, such as glass, silicate, asbestos, wood cellulose, acetylcellulose, polyacrylonitrile, polyester, polyurethane and polyvinyl chloride fibers or mixtures of the same, and also in powders, for example organic or inorganic pigments. With the new pigment there are obtained prints, paint and varnish coatings, coverings, shaped articles, such as sheets, threads, plates, blocks, granulates and rods with a distinct black color in masstone (undiluted form) of excellent durability, and violet color in tint.

The mixtures of substances which contain as active coloring ingredient the black-violet pigment may be of solid, elastic, pasty, viscous, mobile or thixotropic consistency. They may be obtained by conventional methods. Aqueous pastes may be obtained for example by stirring the pigment into water, possibly with the addition of a wetting or dispersing agent or by stirring or kneading the pigment into a dispersing agent in the presence of water and possibly of organic solvents or oils. These pastes may for example be used for the production of flush pastes, printing colors, distempers, plastic dispersions and spinning solutions. The pigment may also be introduced by stirring, rolling, kneading or grinding into water, organic solvents, non-drying oils, drying oils, lacquers, varnishes, plastics or rubber. Finally, it is also possible to work up the pigment by dry mixing with organic or inorganic masses, granulates, fibrous materials, powders and other pigments, to form mixtures of substances.

In addition to its distinct color, jetness of masstone and general fastness, such as fastness to light and weathering and solvent and softener resistance, the pigment is also characterized by resistance to moderately high temperatures. For example, the thermal behavior of the pigment makes it possible to work it into high and low density polyethylene or polypropylene, without the shade of color being substantially dulled by the effect of the temperature during working up.

The following example further illustrates the embodiments of this invention. In this example, all parts given are by weight unless otherwise indicated.

A round-bottom flask equipped with a stirrer, thermometer, nitrogen inlet, and reflux condenser is charged with 22.8 parts of dimethyl succinylsuccinate, 43.4 parts 2-aminobenzophenone, and 300 ml methanol, followed by 0.25 ml concentrated hydrochloric acid. The mixture is stirred under reflux for 8 hours and the precipitated solid separated by filtration from the hot slurry. The resultant solid is washed with methanol and dried. The slightly yellowish product weighs 39.2 parts (71.3%) and is identified as dimethyl 6,13-dihydro-7,14- diphenylbenzo[b]-quinolino-[2,3-j]quinoline-6,13-dicarboxylate.

By way of confirmation of the structure of the intermediate, a small sample is recrystallized from n-butanol and is seen to exhibit the following elemental analysis:
% C=77.7
% H=4.7
% N=4.9

Based on a subsequent determination of its mass spectrum, which shows a molecular ion of 550, the calculated elemental analysis is shown to be:
% C=78.5
% H=4.73
% N=5.09

Its NMR spectrum indicates:
3.53 ppm (6H)
5.20 ppm (2H)
7.2–8.1 ppm (18H)
which is in accord with the assigned structure.

The cyclization reaction is conducted in a round-bottom flask equipped with a stirrer and thermometer charged with 75 parts Dowtherm (eutectic of diphenyl ether and biphenyl) which is brought to reflux. To the boiling solvent is added, portionwise, 5 parts of the intermediate compound over a period of 25 minutes, while allowing generated alcohol to distill out of the reaction mixture. With introduction of the first portion of intermediate, a dark violet solution is formed which upon further addition of intermediate precipitates a nearly black crystalline product at the reaction temperature of 254°–255° C. After completion of the addition, the mixture is refluxed for 15 minutes and cooled to 120° C. The solid is separated by filtration and washed with methanol until the filtrate is colorless. After drying, 3.95 parts (95.4%) of a black, crystalline compound are obtained which does not melt up to 300° C.

Its structure is determined by its mass spectrum which shows a molecular ion of 486, and the following elemental analysis:

| Calculated: | % C = 84.0 | Found: | % C = 83.8 |
|---|---|---|---|
| | % H = 3.70 | | % H = 3.30 |
| | % N = 5.76 | | % N = 5.61 |

When the product is dissolved in concentrated sulfuric acid, the solution exhibits a very strong red fluorescence under ordinary light, and particularly under UV light. When a corresponding sulfuric acid solution of the compound is drowned into water, the resulting slurry shows a fine violet pigment dispersed in dilute acid. When filtered and washed free of acid, the solid can be isolated and dried or flushed into a lithographic varnish.

Alternately, the crude pigment can be particle size reduced by milling in the following manner. Into a laboratory scale ball mill is charged 1500 parts of 1.27 cm diameter steel balls, 150 parts of roofing nails, 135 parts aluminum sulfate pentadecahydrate, 10 parts crude pigment, 3.9 parts perclene and 0.75 parts of isopropyl- amine salt of dodecylbenzenesulfonic acid surfactant. The mill is rotated for 72 hours at approximately 75% of the critical speed. The balls and nails are separated with a screen and the dry powder is added to a stirred solution of 6.9 parts concentrated sulfuric acid in 500 parts water at 50° C. The slurry is stirred and heated to 90±2° C. and kept at this temperature for 1.5 hours. The product is isolated by filtration and washed with hot water until free of acid and sulfate. The product can be dried and then dispersed in a lithographic varnish to assess its pigmentary properties.

The latter are determined utilizing rubout in lithographic varnish prepared with a Hoover Muller. The apparatus is equipped with a ⅛ HP 110-22 V, 60 cycle motor and two glass plates. The muller can be adjusted to stop after 25, 50, 75 or 100 revolutions with 50 revolutions being considered normal. Three weights are used which apply 150 pounds pressure between the plates. In each case, 0.6 parts of dry pigment and 1.2 parts of a lithographic varnish drier are mixed with a spatula on the lower glass plate. The upper plate is locked to the lower plate and the motor is set to stop after fifty revolutions. The plates are separated and the pigment in ink dispersion is picked up and spread out again on the lower plate and the operation repeated six more times. The resulting pigment as an ink dispersion, referred to as the masstone ink, is drawn down versus an appropriate control prepared in the identical manner. In order to assess color strengths of the samples, calculated amounts of the masstone ink (0.18 parts) and a zinc oxide paste dispersion (10 parts) are weighed accurately and mixed with a spatula on a polished glass plate. An appropriate control is prepared in an identical manner. Visual comparison of both the masstones and tints are made wet and after drying at room temperature for several days.

Alternatively, the aqueous press cake can be flushed into the lithographic varnish in order to avoid the drying step and aggregation resulting therefrom.

Upon subjecting the compound to the above procedures, the drawdowns of the lithographic ink masstones and that of the ZnO extensions exhibit distinctive jet black and dark violet colors, respectively. Upon subjecting the drawdowns to exposure in a Fade-O-Meter for 785 hours, the masstone black color is virtually unchanged, while the (tint) extended color shows only a minimal amount of fade It is also to be noted that whereas the isolated crude product is relatively large in particle size, either the milled or the product precipitated from concentrated sulfuric acid is pigmentary in nature.

Summarizing, it is seen that this invention provides a new pigment exhibiting distinctive pigmentary properties. Variations may be made in properties, procedures and materials without departing from the scope of the invention as defined by the following claims.

What is claimed is:

1. 5,15-Diaza-5,15b-dihydrotetrabenzo[a,g,j,p] perylene-6,16-dione.

2. Di($C_1$-$C_3$alkyl) 6,13-dihydro-7,14-diphenylbenzo[b]-quinolino-[2,3-j]quinoline-6,13-dicarboxylate.

3. Dimethyl 6,13-dihydro-7,14-diphenylbenzo[b]-quinolino-[2,3-j]quinoline-6,13-dicarboxylate according to claim 2.

4. A process for preparing the compound of claim 1, which comprises condensing a di($C_1$-$C_3$alkyl) succinylsuccinate with 2-aminobenzophenone at elevated temperatures in the presence of an organic solvent and a catalytic amount of a mineral acid or aliphatic organic acid to form the di($C_1$-$C_3$alkyl) 6,13-dihydro-7,14-diphenylbenzo [b]-quinolino-[2,3-j]quinoline-6,13-dicarboxylate intermediate, cyclizing the intermediate at elevated temperatures and isolating the resulting compound of claim 1.

5. The process of claim 4 which utilizes dimethyl succinylsuccinate, methanol as the organic solvent in the condensation reaction and catalytic amounts of a mineral acid.

* * * * *